United States Patent [19]
Tanaka et al.

[11] Patent Number: 5,432,090
[45] Date of Patent: Jul. 11, 1995

[54] METHOD FOR MEASURING METAL INGREDIENTS IN COMBUSTION GAS

[75] Inventors: Sinji Tanaka, Ibaraki; Shuntaro Koyama, Katsuta; Kenichi Sohma, Ibaraki; Ryoichi Kaneko, Hitachi, all of Japan

[73] Assignee: Hitachi, Ltd., Tokyo, Japan

[21] Appl. No.: 49,294

[22] Filed: Apr. 20, 1993

[30] Foreign Application Priority Data

Apr. 23, 1992 [JP] Japan .................................. 4-104263
Sep. 21, 1992 [JP] Japan .................................. 4-250910

[51] Int. Cl.$^6$ ............................................. G01N 21/72
[52] U.S. Cl. ......................................... 436/79; 436/73; 436/154; 436/171; 436/52
[58] Field of Search ................ 436/79, 73, 153–155, 436/171, 52

[56] References Cited

U.S. PATENT DOCUMENTS 3,088,808  5/1963  Mandell ................................. 436/79
4,896,965  1/1990  Goff et al. ............................ 356/417

FOREIGN PATENT DOCUMENTS 62-9052A  4/1987  Japan .

OTHER PUBLICATIONS

EPRI GS-6485, Project 1654, Aug. 1989, "8th Annual EPRI Conference on Coal Gasification".
"Proceedings of the 6th Annual Coal-Fueled Heat Engines & Gas Stream Cleanup Systems Contractors Review Meeting", Mar. 21–23, 1989, pp. 440–463 & 480–487.

*Primary Examiner*—Lyle A. Alexander
*Attorney, Agent, or Firm*—Antonelli, Terry, Stout & Kraus

[57] ABSTRACT

The invention is to continuously measure the contents of trace ingredients such as alkaline metal contained in combustion gas with high precision. An oxidizer and fuel are supplied into a flue line to form a flame, while a part of the combustion gas is introduced to the flame for inducing light emission. The contents of metal ingredients in the gas are calculated based on the intensity of the emitted light. Since a flame forming device is installed in the flue line without any additional equipment such as a sampling line, and such the contents of trace ingredients in the gas are calculated based on the intensity of the emitted light, the contents of the trace ingredients can be measured with high precision. Quickly responsive monitoring and control are assured.

7 Claims, 7 Drawing Sheets

METHOD FOR MEASURING METAL INGREDIENTS IN COMBUSTION GAS

FIELD OF THE INVENTION

The present invention relates to a method and an apparatus for measuring the contents of metal ingredients contained in combustion gas through an emission spectro-chemical analysis and, more particularly, to a method and an apparatus well suitable for measuring the contents of trace alkaline metals contained in coal combustion gas.

DESCRIPTION OF THE PRIOR ART

Alkaline metals, e.g., sodium (Na) and potassium (K), are contained, though in a very small amount, in combustion gas produced ,When fossil fuel such as coal and petroleum are burnt. Those alkaline metals are extremely highly corrosive and responsible for corrosion of component materials of equipment utilizing such combustion gas. In gas turbines, for example, corrosion of turbine blades is accelerated by the presence of alkaline metals. It is therefore needed to detect the contents of alkaline metals and take any step of reducing the contents.

As disclosed in U.S. Pat. No. 4,896,965, there is known means for determining the contents of alkaline metals in combustion gas, with which a flame is formed by fuel and an oxidizer, the combustion gas is introduced into the flame for causing each of the alkaline metals to emit a specific ray of light, and the intensity of the light emitted from the alkaline metal is determined for calculating its content.

Further, the following methods (1) and (2) are known as means for measuring the contents of trace ingredients in combustion gas.

(1) Metal salt measuring method using flame photometer. This method employs a burner, a monochromator, a photomultiplier, an amplifier, an arithmetic circuit, and a signal display. An analysis is carried out by forming a flame with oxygen or air and hydrogen used as an oxidizer and fuel, respectively, spraying a sample (including various metal salts) directly into the flame through a central flow passage, providing emission spectrum of the flame by the monochromator, introducing the spectrum line of a particular element to the photomultiplier, and taking out the intensity of the spectrum line in proportion to the content of a corresponding metal salt after conversion into an electric signal, thereby measuring the content of the metal salt (see "Spectroscopic Analysis Techniques Using Flames", Chap. 6, pp. 125-152).

(2) Alkali measuring method based on the Ames system and Morgantown Energy Technology Center system (hereinafter referred to METC system). The Ames system employs a burner, a monochromator, and a photomultiplier detector. The METC system utilizes a refractive transmission technique for light using optical fibers. An analytical apparatus comprises a refractive transmission device, a beam separator, an optical filter, a photoelectric transducer, and a data analyzer. With the METC system, an analysis is carried out by forming a flame of oxygen—propane or acetylene—nitrous oxide through a burner, and introducing a small amount of circulating gas generated from Pressurized Fluidized-Bed Combustion (hereinafter referred to as PFBC) to the flame via a sampling line. Then, only metal atoms such as Na and K are separately excited in emission from the flame, and a specific ray of light emitted corresponding to each metal atom is led to the photoelectric transducer for being taken out as an electric signal in proportion to the intensity of atomic radiation, thereby determining the alkali contents (See DOE/METC-89/6101, Proceedings of the Sixth Annual Coal-Fueled Heat Engines and Gas Stream Cleanup Systems Contractors Review Meeting, pp. 442-487).

Any of the above-mentioned prior art methods is intended to measure the alkaline contents by supplying combustion gas as a sample to a flame via a sampling line, providing emission spectrum of the flame, and determining the intensity of spectrum line of each alkali metal contained in the sample. No suggestions are found as to how to sample the combustion gas.

Contents of alkaline metals contained in combustion gas are on the order of ppb at maximum, but even such very small amounts of alkaline metals give rise to a severe influence upon corrosion of component materials of equipment. If a sampling line is provided in a flue, through which combustion gas flow, to draw out a part of the combustion gas for supplying it into a flame, precise content measurement could not be achieved because of the combustion gas at a high temperature condensing water in the sampling line and making the alkaline metals dissolved in the water. There also would rise a possibility that the sampling line might be clogged due to char, ash, etc. contained in the combustion gas.

SUMMARY OF THE INVENTION

An object of the present invention is to provide a method and an apparatus for measuring metal ingredients in combustion gas with which the contents of alkaline metal ingredients in combustion gas can be measured with high precision.

To achieve the above object, the present invention provides a method of measuring metal ingredients in combustion gas, comprising the steps of supplying combustion gas into a flame for causing each of the metal ingredients contained in the gas to emit a specific ray of light, providing emission spectrum in a predetermined range of wavelength to determine the relative intensity of the emitted light, and measuring the content of the metal ingredient emitting the specific ray of light in said predetermined range of wavelength, wherein said combustion gas is held at a temperature higher than the boiling point of the metal ingredient emitting the specific ray of light in said predetermined range of wavelength, and is introduced into said flame for inducing light emission from said metal ingredient.

The position where the flame is to be formed is most preferably in a flue. This enables online measurement of the contents of alkaline metals in combustion gas.

The present invention can be applied to an apparatus for monitoring the contents of alkaline metals in combustion gas of fossil fuel. Other than fossil fuel gas, the present invention can also be utilized to detect the contents of metal ingredients contained in various kinds of gases for the purpose of monitoring. Further, the present invention can be embodied as an apparatus for monitoring the contents of heavy metals such as iron, nickel and chromium.

With means for inducing light emission provided in a flue, it is possible to avoid the problem which has been experienced in the prior art of providing a sampling line and in which a part of metal ingredients in combustion gas disappears midway the sampling line and the detected content is different from the actual content in the combustion gas flowing through the flue.

When a metal ingredient in combustion gas is excited, the excited metal atoms are forced to transit to a lower energy level, whereupon a specific ray of light of wavelength corresponding to the energy gap is emitted. There is correlation between the intensity of the emitted light and the content of the metal ingredient in the combustion gas. Thus, the content of the metal ingredient can be determined by measuring the intensity of the emitted light.

The metal ingredient in combustion gas can be excited by applying a higher energy field than required for the excitation. One of possible exciting means is a flame. For causing the metal ingredient in the combustion gas to emit a specific ray of light inside a fuel through which the gas flows as in the present invention, it is very desirable to form a flame in the flue.

An acetylene (or propane)—oxygen flame, a hydrogen—oxygen flame, etc. can be used as the flame to be formed in the flue. Applicable flames are of course not limited to these ones. It is however desired to employ the hydrogen-oxygen flame which generates no light emitting chemical elements other than O and H, because chemical elements produced in the flame may raise a background level.

A burner is provided in the flue to form a flame and combustion gas is directly sucked into the flame for inducing light emission. A specific ray of light emitted from the flame is sampled and introduced by an optical fiber to the exterior of the flue. Since the light emitted from the flame includes emission spectra of other coexisting metals and emission spectra of the chemical elements, e.g., O and H, a spectrometer such as one utilizing a prism or grating is used to select only the wavelength corresponding to a predetermined metal atom, for example, an alkaline metal atom. The relative intensity of the emitted light is then determined to calculate the content of the metal in the combustion gas.

The content of an alkaline metal in combustion gas changes depending on the temperatures in a combustion furnace. If the content of the alkaline metal in the combustion gas is too high or low as compared with a target value, amounts of an oxidizer and fuel (such as coal, petroleum and gas) supplied to the combustion furnace are controlled based on the detected content of the alkaline metal for adjusting the amount of the alkaline metal generated. Simultaneously, a damage degree of the gas turbine is estimated.

In the present invention, it is desired that a burner for premixing fuel and an oxidizer with each other and jetting the mixture from a nozzle is provided inside a flue through which combustion gas flows, and a flame is formed by the premixed gas.

By forming the flame using the premixed gas of fuel and an oxidizer, the fuel and the oxidizer can be always jetted from the nozzle at a constant mixed ratio, making it possible to keep brightness of the flame constant at all times. As a result, the intensity of the light emitted from the metal introduced to the flame can be measured with high precision.

The combustion gas is desirably supplied to a maximum temperature portion at the center of the flame. To this end, a part of the combustion gas is desirably introduced into the frame through the interior of the burner.

Using a part of the combustion gas as carrier gas for the fuel or the oxidizer supplied to the burner makes it easier to introduce the combustion gas to the center of the flame formed by the burner.

The present invention can be utilized as a preventive maintenance device for a gas turbine driven by combustion gas of fossil fuel. Such a gas turbine is damaged by alkaline metals contained in the combustion gas. By detecting the contents of those alkaline metals, the preventive maintenance of the gas turbine can be achieved.

In combustion apparatus using fossil fuel, a dust collector is often provided midway a flue to remove dust and ash mixed in combustion gas. When applying the present invention to such a combustion apparatus, means for inducing light emission is preferably provided inside the flue downstream of the dust collector.

When an apparatus for monitoring metal ingredients in gas according to the present invention is applied to fossil fuel burning apparatus inclusive of coal gasifying apparatus, or power plants driven by the resulting combustion gas, the monitoring apparatus desirably includes means for indicating the intensity of specific rays of light emitted from the metal ingredients in the gas, or means for indicating the contents of the metal ingredients calculated from the intensity of the emitted light. This enables an operator of the burning apparatus or an operator of the power plant to issue a control signal by knowing the reason why the operation of issuing such a control signal is needed, with the result of remarkably increased reliability.

When indicating the intensity of the emitted light, it is desirable to separately indicate the relationship between the intensity of the emitted light and the content.

The present invention operates as follows in brief. Very small amounts of alkaline metals are contained in combustion gas of coal. If the combustion gas is sampled to measure the contents of those alkaline metals, the temperature of the combustion gas would be so abruptly lowered as to make the alkaline metals deposit onto the wall surface of a sampling line and hence to make it impossible to effect a high-precise measurement. By measuring the contents of the alkaline metals in such a state that the temperature of the combustion gas of coal is held higher than the boiling points of the alkaline metals, deposition of the alkaline metals onto the wall surface can be prevented and, therefore, the contents of the alkaline metals can be measured with high precision.

Providing the flame forming means in the flue, through which the combustion gas flows, enables not only high-precise measurement of the contents of the alkaline metals, but also online measurement thereof.

With the present invention, as a result of so measuring the contents of the alkaline metals in the combustion gas with high precision, a gas turbine or a combustion furnace can be controlled on the basis of the measured results.

A description will now be made of a gas turbine power plant as one example. To precisely measure the contents of trace ingredients in combustion gas generated in a combustion furnace, a plasma torch for producing a flame by fuel (acetylene, hydrogen and propane) and an oxidizer is first installed in a flue at a gas turbine inlet under high-temperature and high-pressure condition. The torch is desirably of the type that cooling water is circulated to cool the outer wall thereof for the purpose of preventing fusion due to the heat. A small amount of the combustion gas containing alkaline metals is sucked into the plasma torch and directly supplied to the plasma flame, causing the alkaline metals to emit specific rays of light. As means for sensing an image of the generated flame, an image sensor with an optical fiber built therein is installed in the flue at a position capable of viewing the torch flame, thereby picking up a flame image. Then, the picked-up light is led by the optical fiber to a spectrometer for providing emission spectra of the alkaline metals.

The spectrometer separates the picked-up light into its spectral components for selecting a particular range of wavelength corresponding to each of the alkaline metals. From the relative intensity of the emission spectrum at the particular wavelength thus separated, the content of each trace ingredient is calculated by using a data processor. The data processor has mechanisms for not only calculating the contents of the trace ingredients, but also displaying a momentary value and an integrated value of the content per trace ingredient.

Based on the analytical results, the contents of the trace ingredients at the gas turbine inlet are monitored and a damage degree of the gas turbine is estimated. Then, an alkaline metal adsorbing unit is disposed in the flue adjacent the gas turbine inlet and operated so that the integrated values of the contents of the alkaline metals are kept within allowable values of the gas turbine. Also, turbine blades of the gas turbine are washed by a cleaning device. Further, amounts of the oxidizer and the fuel (solid powder fuel, petroleum and gas) supplied to the combustion furnace are adjusted to make control for regulating the amounts of the alkaline metals generated.

DESCRIPTION OF PREFERRED EMBODIMENTS

Figure 1:
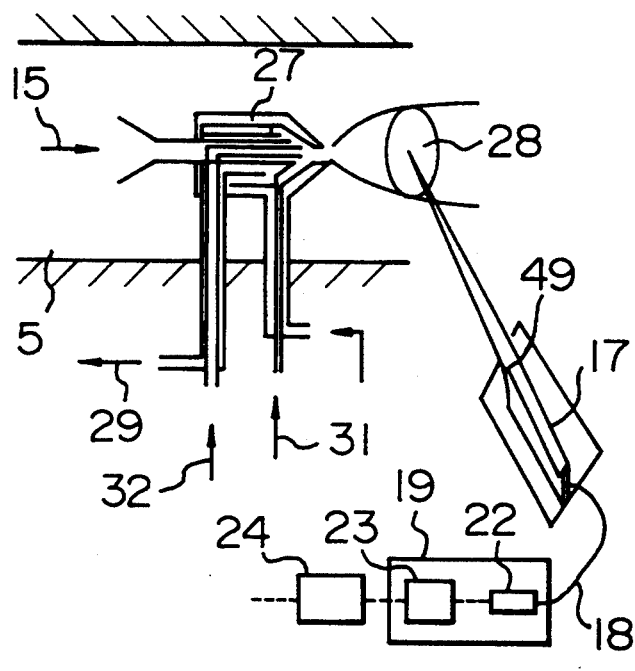
FIG. 1 is a schematic view of a measuring apparatus of the present invention installed in a flue line.

Preferred embodiments of the present invention will be described below with reference to the drawings. FIG. 1 shows the construction of an apparatus for measuring metal ingredients in gas according to the present invention. The measuring apparatus comprises a plasma flame forming device (or a plasma torch) 27 for forming a flame which is provided in a flue 5 at a gas turbine inlet, an optical fiber 17 for sampling light and an optical fiber 18 for transmitting the light, a trace ingredient content calculating device 19 consisted of a spectrometer 22 and a data processor 23, as well as a controller 24.

The plasma torch 27 has the burner structure for producing a combustion flame 28 of acetylene (or propane) and hydrogen or of hydrogen and oxygen, and is of the type that cooling water 29 is circulated to cool the outer wall for the purpose of preventing fusion due to the heat. The plasma torch 27 sucks by itself a small amount of combustion gas 15 containing alkaline metal ingredients and supplies it directly into the flame 28 for generating a plasma flame. The detailed structure of the plasma torch 27 will be described later.

In order to sense an image of the plasma flame 28 in the flue, the sampling optical fiber 17 is installed at a position capable of viewing the plasma flame, to thereby pick up the flame image. The sampling optical fiber 17 is protected by an image guide which is resistant against heat and pressure to avoid any influences by heat, pressure and so forth. The sampling optical fiber 17 has at its distal end a lens system 49 comprising an eyepiece lens, an object lens and others.

The light picked up by the sampling optical fiber 17 is transmitted to the spectrometer 22 by the transmitting optical fiber 18.

Since the light emitted from the flame includes emission spectra of coexisting metals and emission spectra of the chemical elements, e.g., O and H, other than target metal atoms, the trace ingredient content calculating device 19 including the spectrometer 22 and the data processor 23 is used to separate the emitted light into spectral components, select only the emission spectrum corresponding to each of the target metal atoms, and calculate the contents of alkaline metals such as Na and K in the combustion gas based on the relative intensity of the emitted light or the emission spectra. The data processor 23 has mechanisms for not only calculating the contents of the trace ingredients, but also displaying a momentary value and an integrated value of the content per trace ingredient.

Figure 2:
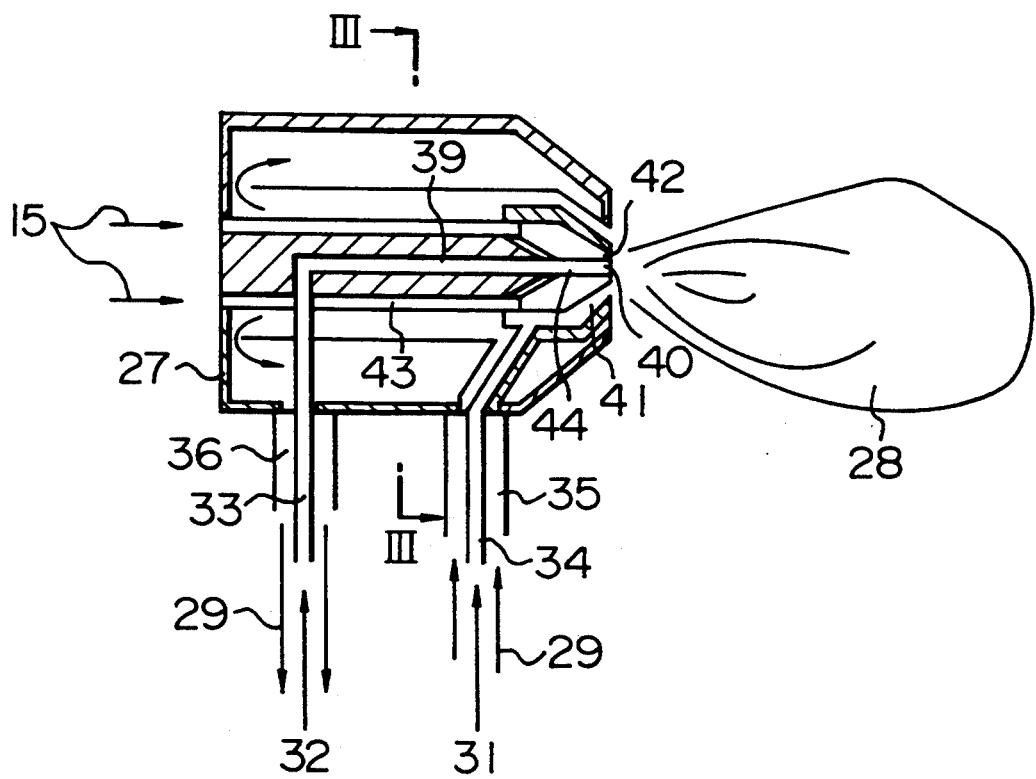
FIG. 2 is a detailed axial sectional view of a plasma torch of the present invention.
Figure 3:
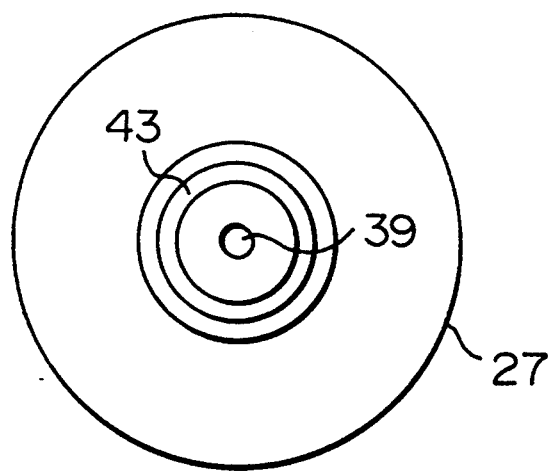
FIG. 3 is a sectional view of the plasma torch taken along line III—III in FIG. 2.
Figure 4:
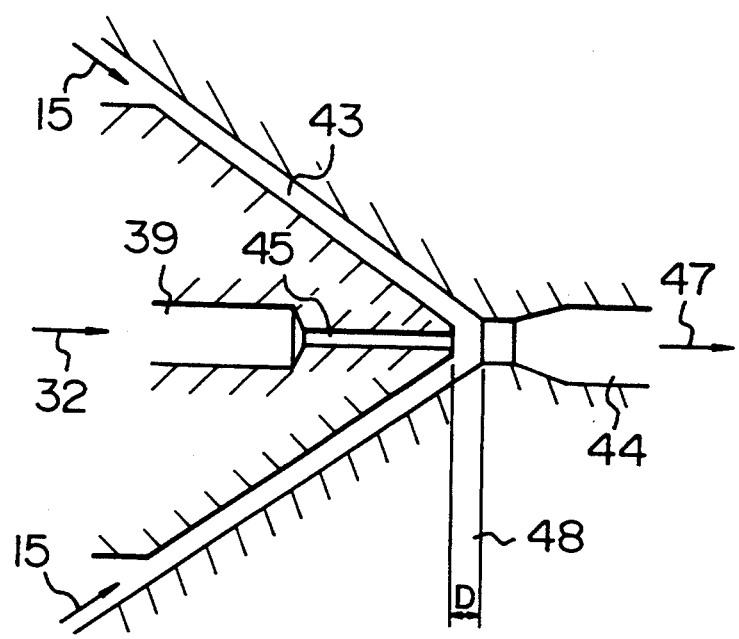
FIG. 4 is a detailed sectional view of a merging portion of fuel and combustion gas in the plasma torch.

The details of the plasma torch of the present invention will now be described with reference to FIGS. 2, 3 and 4.

The cooling water 29 is circulated, as mentioned above, to cool the outer wall of the plasma torch 27 for the purpose of preventing fusion due to the heat. The circulating water is supplied through a cooling water inlet 35 defined by an outermost tube and then discharged through an outlet line 36. Fuel (such as hydrogen, to acetylene or propane) 32 flows through a central passage 39 defined by an innermost tube and is jetted out of a spray hole 40 provided at the torch distal end.

An oxidizer (such as oxygen or air) 31 is supplied to an oxidizer flow passage 41 via an oxidizer supply line 34 and then jetted out of an oxidizer spray hole 42 at the torch distal end.

The combustion gas (produced gas) 15 is sucked to flow through a combustion gas flow passage 43 for contacting the fuel (such as hydrogen, acetylene or propane) 32 coming through the central passage 39 defined by the innermost tube in an outlet region at the nozzle distal end inside the torch 27. Details of the region where the combustion gas (produced gas) 15 contacts the fuel (such as hydrogen, acetylene or propane) 32 is shown in FIG. 4.

The fuel (such as hydrogen, acetylene or propane) 32 is forced to flow through the central passage 39 defined by the innermost tube and to jet out of a fuel flow passage 45 within the nozzle at a high flow speed (greater than 150 m/s). Such a high flow speed produces a partial vacuum slightly lower than the atmospheric pressure, and the combustion gas (produced gas) 15 is sucked from the combustion gas flow passage 43 due to the partial vacuum so that the combustion gas (produced gas) 15 is sprayed out of a fuel/produced gas mixture line 47 together with the fuel (such as hydrogen, acetylene or propane) 32.

Figure 8:
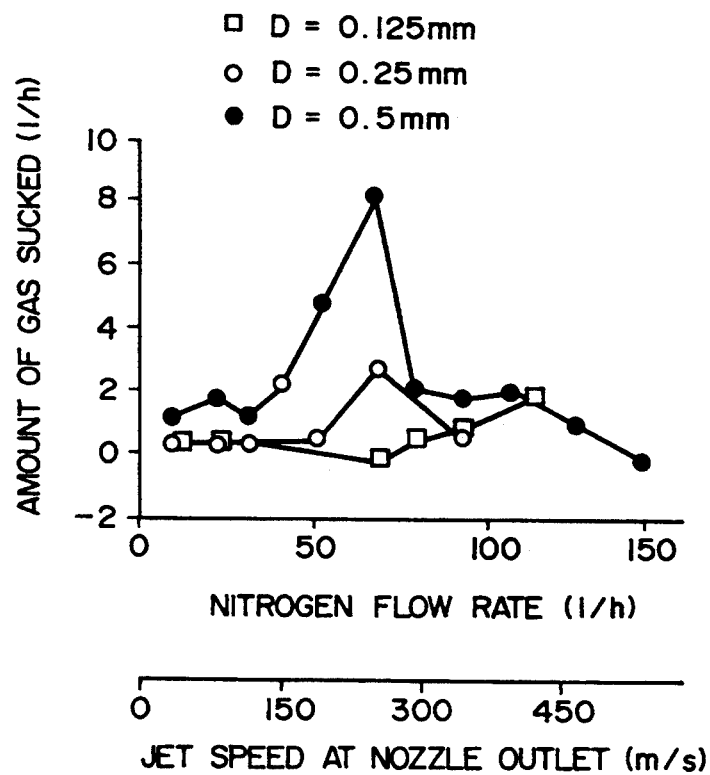
FIG. 8 is a graph showing gas suction characteristics of the plasma torch.

FIG. 8 shows gas suction characteristics of the plasma torch. Specifically, the graph indicates the amount of gas sucked through the combustion gas flow passage 43 as resulted when the fuel is forced to flow (while changing from 10 l/h to 140 l/h) and the distance D at an end 48 of a nozzle 44 in FIG. 4 is changed from 0.125 mm to 0.5 mm. As seen from FIG. 8, the gas suction characteristics are dependent on the flow rate of the fuel and the size of the distance D as follows. When the distance D is 0.125 mm, the combustion gas was hardly sucked until the flow rate of the fuel reaches 60 l/h, but the gas suction began from 70 l/h. When the distance D is 0.25 mm, the combustion gas of 3 l/h was sucked at the fuel flow rate of 70 l/h. When the distance D is 0.5 mm, the amount of the sucked combustion gas was maximized to be about 8 l/h at the fuel flow rate of 70 l/h. Therefore, the combustion gas is satisfactorily sucked when the distance D is in a range of 0.25 to 0.5 mm and the fuel flow rate is in a range of 40 to 80 l/h. The nozzle spray speed under that condition is in a range of 150 m/s to 300 m/s. In view of the above, the distance D and the flow rate of the fuel (such as hydrogen, acetylene or propane) 32 are constantly set to 0.5 mm and 70 l/h, respectively.

A description will now be given of another embodiment in which an apparatus for monitoring the contents of trace ingredients according to the present invention is installed in the flue 5 of the combustion furnace to measure the contents of alkaline ingredients in the combustion gas 15 for controlling a burning condition of the combustion furnace and estimating a damage degree of the gas turbine.

Figure 5:
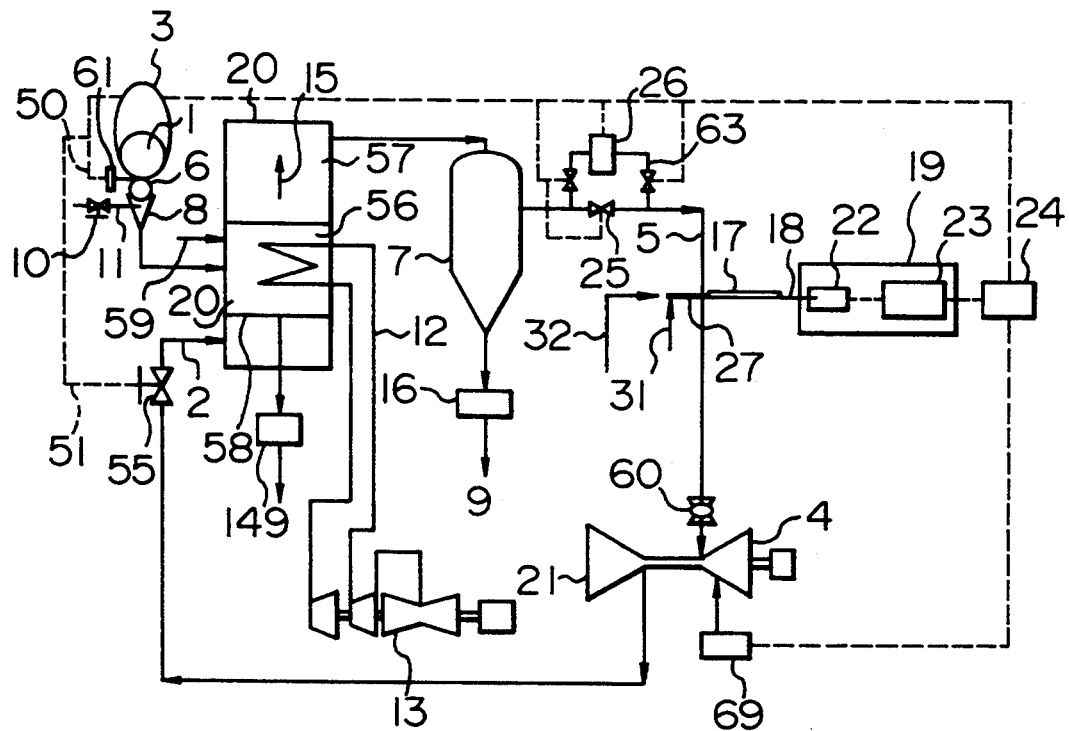
FIG. 5 is a schematic view of a composite cycle power plant utilizing Pressurized Fluidized-Bed Combustion (PFBC) which incorporates the measuring apparatus of the present invention.

FIG. 5 shows a composite cycle power plant using Pressurized Fluidized-Bed Combustion (PFBC). Powdered coal 1 is filled in a supply hopper 3. After setting a pressure in the supply hopper 3 to be slightly higher than a pressure in a combustion furnace (such as a PFBC boiler, a gas gasifying furnace and a boiler) 20, the powdered coal 1 is delivered by a feeder 6 in a predetermined amount at a time and supplied into an ejector 8, following which by setting the flow rate of carrier gas to a predetermined value by an adjusting valve 10 and supplying the carrier gas through a carrier gas line 11, the powdered coal 1 is introduced to a PFB forming portion 56 in the combustion furnace 20 with airborne streams. Thus, the powdered coal 1 is transported by air at this time.

The combustion furnace 20 is of the PFBC type and serves as a PFBC boiler having a heat conducting tube 12 for adjusting the temperature. The combustion furnace 20 includes the heat conducting portion 12, the PFB forming portion 56, an air tower portion 57, and an air dispersing mechanism 58. Combustion air 2 is introduced from a gas turbine air compressor 21 (described later) to flow through an oxidizer (air) flow rate adjusting valve 55 for adjustment of the gas flow rate, followed by being supplied to a lower portion of the air dispersing mechanism 58 in the combustion furnace 20.

The PFB forming portion 56 is set to an air rich condition with the furnace temperature of about 800° to 900° C., the furnace pressure of about 10 to 16 $kg/cm^2G$, thereby perfectly burning the powered coal 1. The produced combustion gas 15 flows upward. Accordingly, the combustion gas contains oxygen of about 2 to 5%. In addition, limestone 59 is separately supplied into the combustion furnace 20 and, at the same time, air is sprayed in multiple stages to thereby achieve both desulfurization and reduction in nitrogen oxides simultaneously.

Combustion ash (or char) 9 is extracted out of the bottom of the combustion furnace 20 into an ash recovery unit 14. Water vapor generated from the heat conducting tube 12 is utilized to operate a steam turbine 13.

Since the combustion gas 15 contains a small amount of the ash 9, a dust collector 7 such as a cyclone (e.g., a bug filter or multi-cyclone) is installed in a line downstream of the combustion furnace 20 to remove the ash 9 which is then extracted into a char recover unit 16. The combustion gas 15 flows through the flue line 5 and is supplied to a gas turbine 4. In a bypass line 63 branching from an outlet of the dust collector 7, there are provided an alkaline metal adsorbing unit 26 and directional control valves 25. A fuel gas amount adjusting valve 60 is provided at an inlet of the gas turbine 4. Further, the gas turbine 4 is associated with a blade washing control mechanism 69 for washing turbine blades.

At the inlet of the gas turbine 4 midway the flue line 5, there are provided the flame forming plasma torch 27, the sampling optical fiber 17, the transmitting optical fiber 18, the trace ingredient content calculating device 19 including the spectrometer 22 and the data processor 23, and the controller 24 all mentioned above. The sampling optical fiber 17 is installed at a position downstream of the dust collector such as the cyclone, whereby an influence by powdery granules such as dust containing carbon not yet burned up is made so small as to avoid clouding or the like at the distal end of the optical fiber due to the powdery granules and enable satisfactory image sensing.

Figure 9:
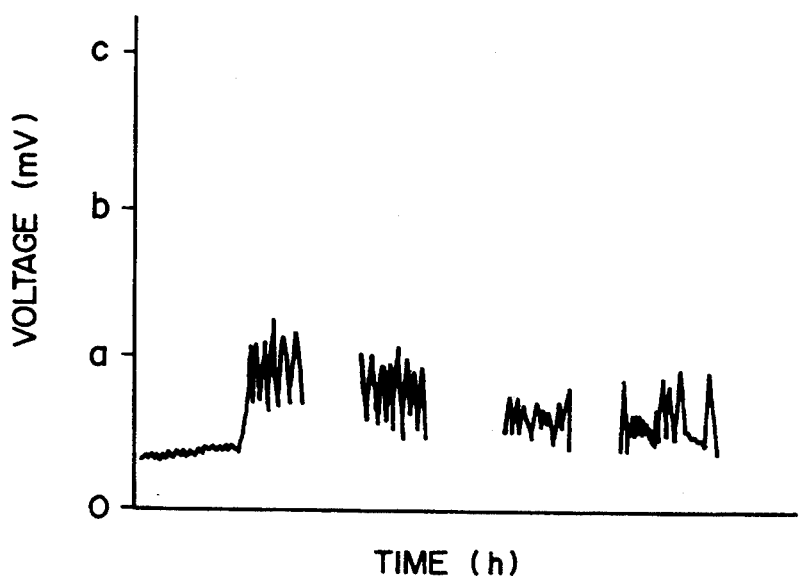
FIG. 9 is a graph showing the result of Na detection by a spectrometer when a simulated liquid is supplied.
Figure 10:
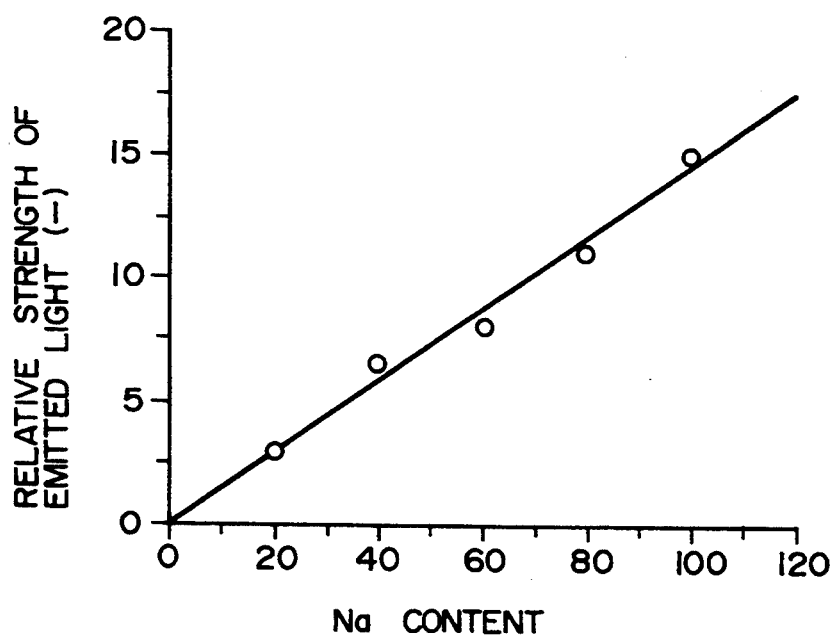
FIG. 10 is a graph showing the relationship between the relative intensity of emitted light and the Na content.

In the plant constructed above, the content of an alkaline ingredient was measured by setting the supply amount of the powdered coal 1 to be constant but changing the flow rate of the air 2. Specifically, by setting the temperature in the flue 5 to be constant at 850° C. and flowing oxygen and $C_3H_8$ for the torch at respective flow rates of 0.5 $Nm^3/h$ and 0.07 $Nm^3/h$, the powdered coat 1 is supplied into the furnace after igniting it. The resulting result of Na detection is shown in FIG. 9. Thus, the graph of FIG. 9 indicates the result of detecting the Na content when the detection wavelength for Na is set to 585.5 nm. The horizontal axis represents a supply time (h) and the vertical axis represents a level of voltage (mV). As seen from FIG. 9, as the Na content increases, the voltage level is raised. In the above measurement, Na cannot be detected if the detection wavelength is shifted from the target one even to a small extent. Also, FIG. 10 shows the result of converting the voltage level obtained from the above result into the relative intensity of the emitted light (i.e., indicated voltage level/voltage level at alkali 0 base). The horizontal axis represents the Na content (ppm) and the vertical axis represents the relative intensity of the emitted light (−). As seen from FIG. 10, the relative intensity of the emitted light was about 3 when the Na content was 20 ppm, while the relative intensity of the emitted light was about 11 when the Na content was 80 ppm. Thus, there is correlation between the Na content and the relative intensity of the emitted light. In the above analysis of the Na content, the combustion gas was sampled from the flue and introduced to an analyzer, thereby measuring the Na content in a batch manner.

Figure 11:
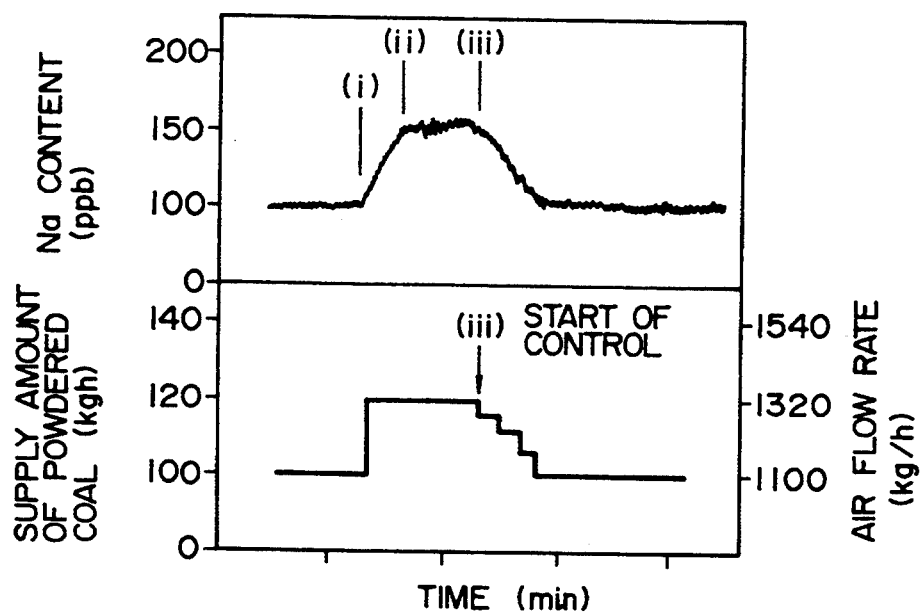
FIG. 11 is a graph showing the result of controlling the Na content with respect to a supply amount of powdered coal and a flow rate of air.

As an advanced application of the above, the burning condition was controlled to be kept constant by detecting the contents of the trace ingredients in the combustion gas 15 flowing through the flue 5 and adjusting both the amount of the powdered coal 1 and the flow rate of the air 2 supplied to the combustion furnace 20. Then, changes in the Na content and operating states for control were confirmed when the plant is normally operated with the supply amount of the powdered coal and the air flow rate both kept constant, while varying the load. The results are shown in FIG. 11. The horizontal axis represents the elapsed time and the vertical axis represents the Na content, as well as the supply amount of the powdered coal and the air flow rate. In FIG. 11, (i) indicates the time at which the load was forcibly increased 1.2 times. This abruptly raised the Na content as indicated by (ii). Therefore, the controller 24 was actuated at the time (iii) to make control for reducing the Na content, by transmitting signals 50, 51 to a fuel flow rate control mechanism 61 and the oxidizer flow rate adjusting valve 55, respectively, so that the supply amount of the powdered coal and the air flow rate were changed while changing the ratio of the air flow rate to the supply amount of the powdered coal (hereinafter referred to as the air ratio) at a constant rate. As a result, the load was stepwisely lowered and the Na content was gradually reduced, as shown in FIG. 11. Finally, the Na content fell down to the original target value.

In other words, upon the Na content being changed momentarily, the operator actuates the controller 24 for transmitting the signals 50, 51 to the oxidizer flow rate adjusting valve 55 through which the oxidizer is supplied to the lower portion of the combustion furnace 20 and the fuel flow rate control mechanism 61 for changing a rotational speed of the feeder 7 to adjust the supply amount of the powdered coal, respectively, thereby varying the air ratio through their operation. Based on the air ratio (it is generally known that the furnace temperature increases at the larger air ratio), the burning condition of the combustion furnace 20 is controlled to suppress the amounts of the trace ingredients generated.

Next, mechanisms for controlling the combustion furnace 20 and the gas turbine 4 based on the content of a trace ingredient will be described in detail with reference to FIGS. 12 and 13.

Figure 12:
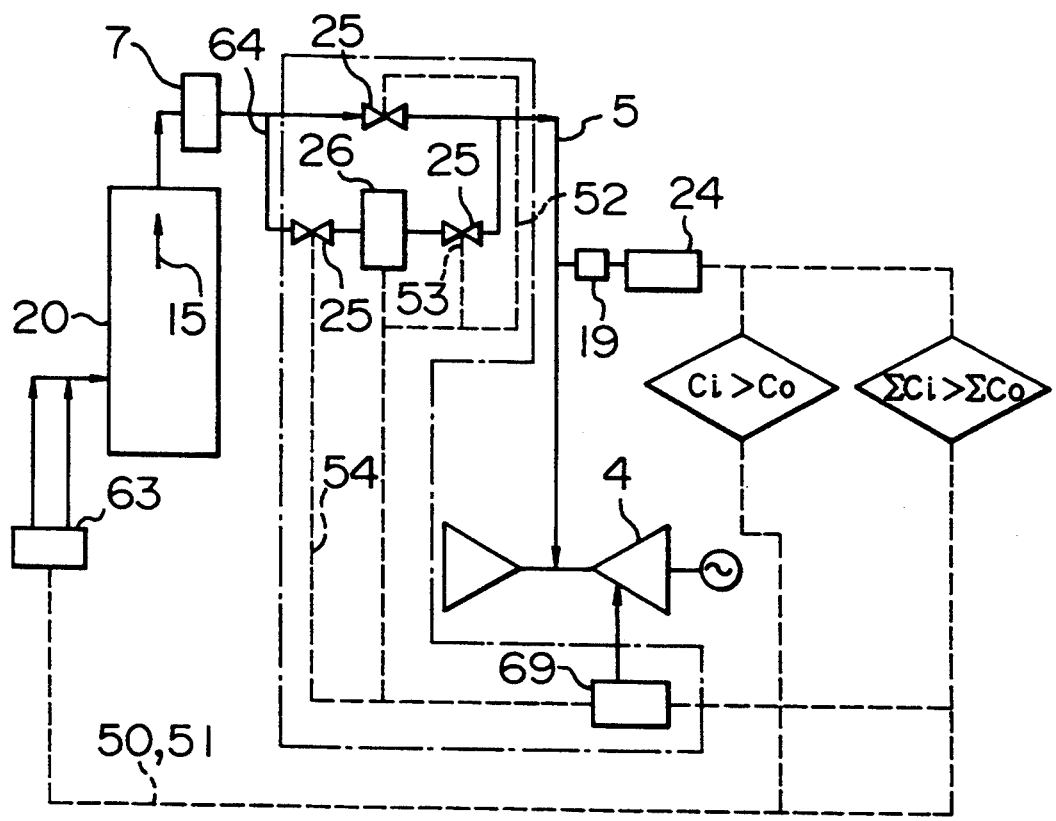
FIG. 12 is a schematic view showing a system for controlling a combustion furnace and a gas turbine based on the metal contents in gas.
Figure 13:
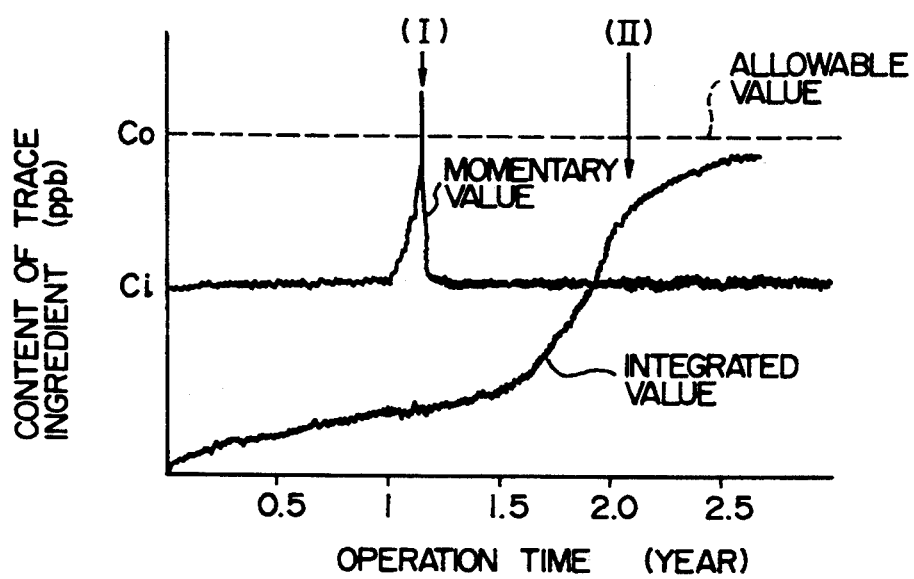
FIG. 13 is a graph showing the relationship of a momentary value and an integrated value of the Na content with respect to an operation time.

FIG. 12 shows details of the mechanisms for controlling the combustion furnace 20 and the gas turbine 4 based on the content of a trace ingredient. The illustrated system includes the alkaline metal adsorbing unit 26, the blade washing control mechanism 69, the directional control valves 25, as well as a combustion fuel control mechanism 63. FIG. 13 shows changes in the content of the trace ingredient. The horizontal axis represents an operation time and the vertical axis represents an integrated value and a momentary value of the Na content. In the case (I) where the momentary value $C_i$ of the Na content abruptly increases above an allowable content $C_o$, this is judged to be due to a change in the burning condition of the combustion furnace 20, and the controller 24 is actuated to transmit the signals 50, 51 to the combustion furnace control mechanism 63 so that the fuel amount and the flow rate of the oxidizer are controlled to lower the Na content. In the case (II) where the integrated value $vC_i$ of the Na content approaches an allowable content $vC_o$, the following control operation is performed on the gas turbine side for protecting the gas turbine 4, in addition to the above control operation on the side of the combustion furnace 20. The controller 24 transmits signals 52, 53, 54 to the respective directional control valves 25 to open the valves provided in a bypass line 64 for changing a flow line of the combustion gas 15. The combustion gas 15 is thereby forced to flow through the alkaline metal adsorbing unit 26 provided in the bypass line 64, so that the trace ingredient is adsorbed by an alkali adsorbent filled in the alkaline metal adsorbing unit 26 to reduce the content of the alkaline ingredient. Also, a signal is transmitted to the blade washing control mechanism 69 associated with the gas turbine 4 for washing the turbine blades, whereupon the operation of washing out the trace ingredient deposited onto the turbine blades is performed.

Figure 6:
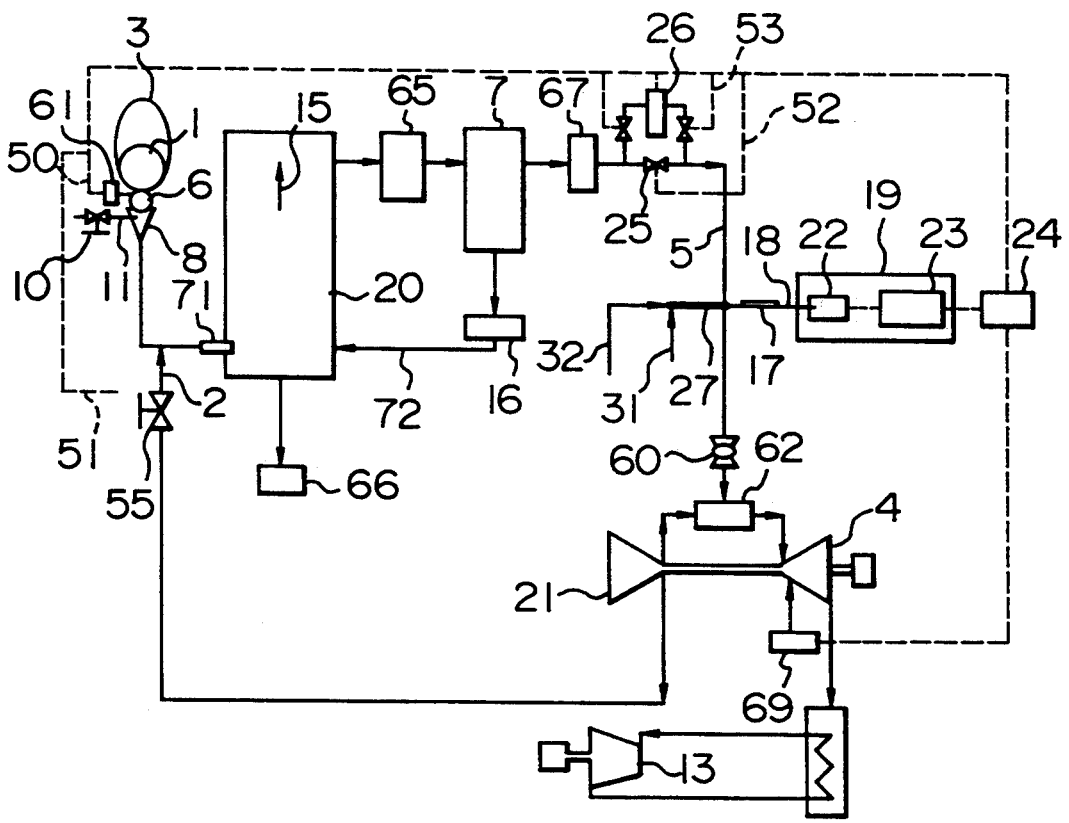
FIG. 6 is a schematic view of a composite coal gasification power plant which incorporates the measuring apparatus of the present invention.

FIG. 6 shows another embodiment in which the present invention is applied to a power plant combined with coal gasification. This plant is different from that of FIG. 5 in that a burning unit 62 is installed at the inlet of the gas turbine 4 because the pressure is as high as 30 atg, the furnace temperature is also as high as 1600° C., and gas with $H_2$ and CO being rich is produced from the gasifying reaction. Further, in addition to a dust collector 7, a waste heat recovery unit 65 and a desulfurizing unit 67 are installed on the outlet side of a coal gasifying furnace 20. The construction of this plant will be described below in brief.

Powdered coal 1 is filled in a supply hopper 3. After setting a pressure in the supply hopper 3 to be slightly higher than a pressure in a gasifying furnace 20, the powdered coal 1 is delivered by a feeder 6 in a predetermined amount at a time and supplied into an ejector 8, following which the powdered coal 1 is introduced to the gasifying furnace 20 with airborne streams via a burner 71 associated with the gasifying furnace 20 in a dry supply manner.

The gasifying furnace 20 is of the jet stream bed type that provides a higher gasifying reaction, easier load fluctuations, the simpler structure and a greater capacity than the PFBC type. In the gasifying furnace 20, the powdered coal 1 and char containing carbon not yet burned are burnt at a high temperature (above 1600° C.) to produce high-temperature combustion gas. At the outlet of the gasifying furnace 20, the waste heat recovery unit 65 is provided for recovering the waste heat. Also, since coal ash is molten to produce slug in the gasifying furnace 20 because of high temperature, the molten slug is dropped into a slug hopper 66, installed below the gasifying furnace 20, to be quickly solidified and then discharged.

Gasifying air 2 is introduced from a gas turbine air compressor 21 to flow into an oxidizer (air) flow rate adjusting valve 55 from which the air 2 is supplied into the gasifying furnace 20 via the burner 71 after being adjusted in its flow rate. The gasifying air 2 is contacted with the powdered coal 1 for reaction in an outlet region at the distal end of the burner 71.

Since produced gas 15 includes char containing carbon not yet burned up, the dust collector 7 such as a cyclone (or a bug filter) is installed in an outlet line of the gasifying furnace to recover the char so that the recovered char is passed through a char supply line 72 and supplied into the gasifying furnace 20 again with pre-airborne streams. Also, since the produced gas 15 includes a small amount of $H_2S$, the produced gas 15 is passed through the desulfurizing unit 67, causing the cleaned gas to flow through the flue line 5 for supply to the burning unit 62 installed at the inlet of the gas turbine 4. The remaining is the same as the plant of FIG. 5.

Figure 7:
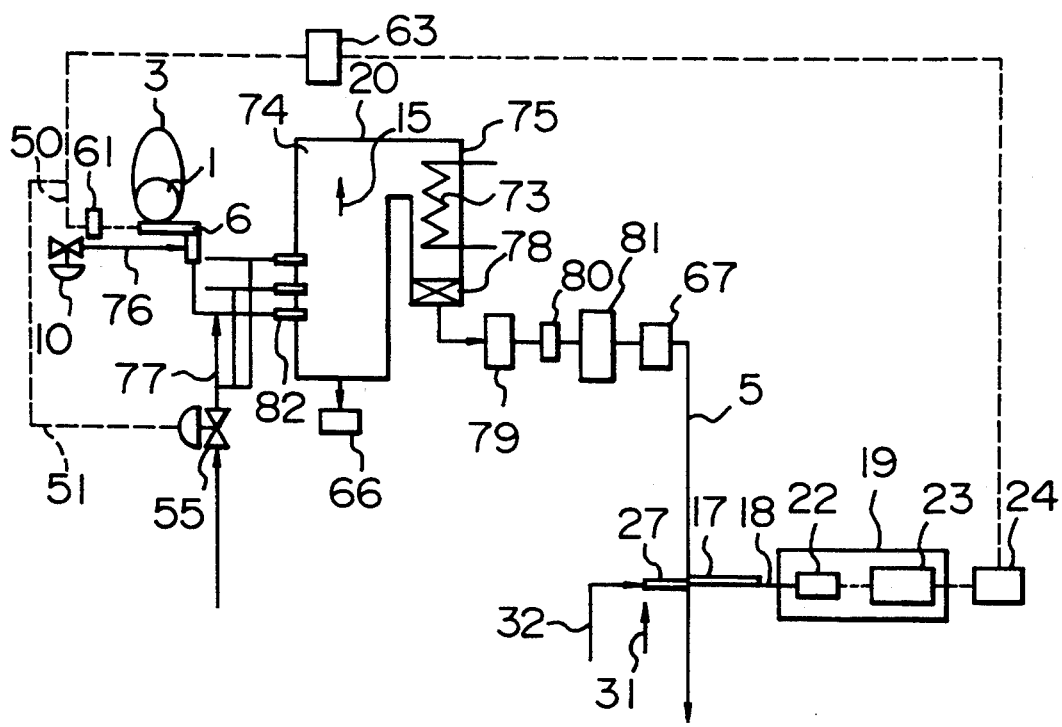
FIG. 7 is a schematic view of another power plant which incorporates the measuring apparatus of the present invention.

FIG. 7 shows another power plant in which the present invention is applied to a powdered coal boiler. The construction of this plant will be described below in brief.

Powdered coal 1 is stored in a supply hopper 3 and delivered by a feeder 6 in a predetermined amount at a time depending on the load. Then, the powdered coal 1 is transported with airborne streams by using primary air 76 for burning and supplied into the combustion furnace 20 via a burner 82 associated with the combustion furnace 20.

Secondary air 77 for burning flows into an oxidizer (air) flow rate adjusting valve 55 and is then supplied into the combustion furnace 20 via the burner 82 after being adjusted in its flow rate. The secondary air 77 for burning is contacted with the powdered coal 1 in an outlet region at the distal end of the burner 82. The burner 82 is of the premixing type.

The combustion furnace 20 comprises a combustion chamber 74, a superheater 75 and a coal saving unit 78. The combustion furnace 20 is of the slug tapping type that coal ash is taken out in a molten state. The burner 82 is arranged plural in number along a side wall of the combustion chamber, and the powdered coal 1 collide with each other in a central portion to be burnt at a high temperature above 1700° C. Since the coal ash is molten because of the high temperature and fallen down in a fluidized state into a slug hopper 66, installed below the combustion furnace 20 and filled with water, to be quickly solidified into granules and then discarded. Thereafter, the combustion gas 15 flows into a section where the superheater 75 comprising a radiation conducting area 73 provided with bare tubes and the coal saving unit 78 are installed. The superheater 75 evaporates moisture contained in the gas (vapor) 15 and further superheats the entire gas for creating a superheated vapor. The coal saving unit 78 preheats water supplied to the boiler by utilizing the surplus heat of the gas 15.

On the outlet side of the combustion furnace 20, there are installed a deninrating unit 79, an air preheater 80, an electric dust collector 81, and a desulfurizing unit 67. The gas 15 flowing out of the furnace 20 is first supplied to the denitrating unit 79 for removing nitride oxides such as NOx), followed by flowing into the air preheater (which preheats air 77 supplied to the furnace 20 by utilizing the surplus heat of the combustion gas 15) 80. Since the gas 15 contains dust and other foreign matters, it is passed through the electric dust collector 81 for removing them. Further, since the gas 15 contains hydrogen sulfide etc. as environment contaminating substances, it is then supplied to the desulfurizing unit 67 for removing them.

After that, the contents of trace ingredients are detected by the metal ingredient monitoring apparatus of the present invention, which is installed in the flue line 5, to monitor the burning condition in the boiler. When the contents of trace ingredients abruptly changes, control operation is made to change the air ratio for protecting the boiler.

While the present invention is applied to the PFBC boiler, the gasifying apparatus, the powdered coal burning apparatus, etc. in the above embodiments, the present invention is not limited to those embodiments. The present invention can be of course applicable to other facilities such as coal liquefying apparatus, dry distillating apparatus and fuel cells as well.

With the present invention, the contents of metals contained in gas in very small amounts can be continuously and quickly measured with high precision. Since the means inducing light emission to measure the metal contents in gas is provided in the flue downstream of the dust collector, it is possible to avoid contamination in the combustion gas flow passage in the torch, enable analysis on the contents of trace ingredients, and further achieve highly responsive monitoring and control.

In short, according to the present invention, the gas flowing through the flue is directly sampled and subjected to light emission without providing any sampling line, and the contents of metals contained in the gas are measured from the intensity of the emitted light. As a result, the ingredients in very small amounts can be measured with high precision.

What is claimed is:

1. A method of measuring metal ingredients in combustion gas, comprising the steps of:

placing a burner for burning a fuel by the aid of an oxidizer to form a plasma flame in a flue through which combustion gas flows, said burner having formed therein a fuel passage for said fuel, an oxidizer passage for said oxidizer, a combustion gas passage for said combustion gas and a junction between said fuel passage and said combustion gas passage;

supplying said fuel into said burner at a substantially constant rate to cause said combustion gas to be sucked into said burner by suction at a substantially constant rate;

supplying the sucked said combustion gas into said plasma flame of said burner for causing each of metal ingredients contained in said combustion gas to emit a specific ray of emitted light, providing emission spectrum in a predetermined range of wavelength to determine a relative intensity of said emitted light, and using said relative intensity for measuring a content of said metal ingredients emitting said emitted light in said predetermined range of wavelength, wherein said combustion gas is held at a temperature higher than a boiling point of said metal ingredients emitting said emitted light in said predetermined range of wavelength, and using a measured said content of said metal ingredients in said combustion gas to control a supply of a furnace fuel into a furnace from which said combustion gas flows into and through said flue.

2. A method of measuring metal ingredients in combustion gas, comprising the steps of:

placing a burner for burning a fuel by the aid of an oxidizer to form a plasma flame in a flue through which combustion gas flows, said burner having formed therein a fuel passage for said fuel, an oxidizer passage for said oxidizer, a combustion gas passage for said combustion gas and a junction between said fuel passage and said combustion gas passage;

supplying said fuel into said burner at a substantially constant rate to cause said combustion gas to be sucked into said burner by suction at a substantially constant rate;

supplying the sucked said combustion gas into said plasma flame of said burner for causing each of metal ingredients contained in said combustion gas to emit a specific ray of emitted light, providing emission spectrum in a predetermined range of wavelength to determine a relative intensity of said emitted light, and using said relative intensity for measuring a content of said metal ingredients emitting said emitted light in said predetermined range of wavelength, wherein said plasma flame is formed in a flue through which said combustion gas flows to thereby induce light emission from a part of said combustion gas in said flame, and using a measured said content of said metal ingredients in said combustion gas to control a supply of a furnace fuel into a furnace from which said combustion gas flows into and through said flue, wherein said combustion .gas is held at a temperature higher than a boiling point of said metal ingredients emitting said emitted light in said predetermined range of wavelength.

3. A method of measuring metal ingredients in combustion gas, comprising the steps of:

placing a burner for burning a fuel by the aid of an oxidizer to form a plasma flame in a flue through which combustion gas of fossil fuel flows, said burner having formed therein a fuel passage for said fuel, an oxidizer passage for said oxidizer, a combustion gas passage for said combustion gas and a junction between said fuel passage and said combustion gas passage;

supplying said fuel into said burner at a substantially constant rate to cause said combustion gas to be sucked into said burner by suction at a substantially constant rate;

supplying the sucked said combustion gas of fossil fuel into said plasma flame of said burner to induce light emission, providing emission spectrum in a range of wavelength corresponding to each of said metal ingredients in said plasma flame to determine a relative intensity of said emitted light, using said relative intensity for measuring a content of said metal ingredients in said plasma flame, wherein said plasma flame is formed in a flue through which said combustion gas flows, and is formed by fuel and an oxidizer both supplied externally of said flue for thereby inducing light emission from a part of said combustion gas in said plasma flame, and said emitted light is led out of said flue to produce emission spectrum in a range of wavelength corresponding to each of said metal ingredients for determining a relative intensity of said emission spectrum, and using a measured said content of said metal ingredients in said combustion gas to control a supply of a furnace fuel into a furnace from which said combustion gas flows into and through said flue, wherein said combustion gas is held at a temperature higher than a boiling point of said metal ingredients emitting said emitted light in said range of wavelength.

4. A method according to claim 3, wherein said metal ingredients are alkaline metal ingredients.

5. A method of measuring metal ingredients in combustion gas, comprising the steps of:

placing a burner for burning a fuel by the aid of an oxidizer to form a plasma flame in a flue through which combustion gas of fossil fuel flows said burner having formed therein a fuel passage for said fuel an oxidizer passage for said oxidizer, a combustion gas passage for said combustion gas and a junction between said fuel passage and said combustion gas passage, supplying said fuel into said burner at a substantially constant rate to cause said combustion gas to be sucked into said burner by suction at a substantially constant rate:

supplying the sucked said combustion gas of fossil fuel into said plasma flame of said burner to induce light emission.

providing emission spectrum in a range of wavelength corresponding to each of said metal ingredients in said plasma flame to determine a relative intensity of said emitted light, using said relative intensity for measuring a content of said metal ingredients in said plasma flame, wherein said plasma flame is formed in a flue through which said combustion gas flows, and is formed by fuel and an oxidizer both supplied externally of said flue for thereby inducing light emission from a part of said combustion gas in said plasma flame, and said emitted light is led out of said flue to produce emission spectrum in a range of wavelength corresponding to each of said metal ingredients for determining a relative intensity of said emission spectrum, and using a measured said content of said metal ingredients in said combustion gas to control a supply of a furnace fuel into a furnace from which said combustion gas flows into and through said flue, wherein said plasma flame is formed at a location where a temperature of said combustion gas in said flue is held higher than a boiling point of said metal ingredients.

6. A method of measuring metal ingredients in combustion gas, comprising the steps of:

placing a burner for burning a fuel by the aid of an oxidizer to form a plasma flame in a flue through which combustion gas flows, said burner having formed therein a fuel passage for said fuel, an oxidizer passage for said oxidizer, a combustion gas passage for said combustion gas and a junction between said fuel passage and said combustion gas passage;

supplying said fuel into said burner at a substantially constant rate to cause said combustion gas to be sucked into said burner by suction at a substantially constant rate, wherein there is an exciting of a pan of said combustion gas flowing through a flue by said plasma flame formed in said flue to form emitted light corresponding to metal ingredients from said combustion gas, measuring contents of metal ingredients contained in said combustion gas based on positions and intensities of spectrum lines of said emitted light, and using a measured said content of said metal ingredients in said combustion gas to control a supply of a furnace fuel into a furnace from which said combustion gas flows into and through said flue, wherein said combustion gas is held at a temperature higher than a boiling point of said metal ingredients emitting said emitted light in said a predetermined range of wavelength.

7. A method of measuring metal ingredients in combustion gas, comprising the steps of:

placing a burner for burning a fuel by the aid of an oxidizer to form a plasma flame in a flue through which combustion gas flows, said burner having formed therein a fuel passage for said fuel, an oxidizer passage for said oxidizer, a combustion gas passage for said combustion gas and a junction between said fuel passage and said combustion gas passage;

supplying said fuel into said burner at a substantially constant rate to cause said combustion gas to be sucked into said burner by suction at a substantially constant rate, thus branching a part of said combustion gas flowing through said flue from said flue, supplying the thus branched said combustion gas to said plasma flame while substantially holding a temperature of said combustion gas constant, providing emission spectrum in an at least one predetermined range of wavelength from said plasma flame to determine a relative intensity of said emission spectrum, measuring a content of metal ingredients emitting said emitted light in said predetermined range of wavelength from said relative intensity of said emission spectrum, and using a measured said content of said metal ingredients in said combustion gas to control a supply of a furnace fuel into a furnace from which said combustion gas flows into and through said flue, wherein said combustion gas is held at a temperature higher than a boiling point of said metal ingredients emitting said emitted light in said predetermined range of wavelength.

* * * * *